United States Patent
Gao et al.

(10) Patent No.: US 7,629,881 B2
(45) Date of Patent: Dec. 8, 2009

(54) SENSOR-BASED ADAPTIVE WEARABLE DEVICES AND METHODS

(75) Inventors: Tia Gao, Ellicott City, MD (US); William E. Bishop, Baltimore, MD (US); Radford R. Juang, Irvine, CA (US); Alexander M. Alm, Rockville, MD (US); David M. White, Silver Spring, MD (US); David A. Crawford, Silver Spring, MD (US); Steven M. Babin, Greenbelt, MD (US); Jeffrey S. Chavis, Ellicott City, MD (US)

(73) Assignee: The Johns Hopkins University, Baltimore, MD (US)

( * ) Notice: Subject to any disclaimer, the term of this patent is extended or adjusted under 35 U.S.C. 154(b) by 367 days.

(21) Appl. No.: 11/741,756

(22) Filed: Apr. 29, 2007

(65) Prior Publication Data

US 2008/0055074 A1    Mar. 6, 2008

Related U.S. Application Data

(60) Provisional application No. 60/795,815, filed on Apr. 28, 2006, provisional application No. 60/849,570, filed on Oct. 5, 2006, provisional application No. 60/828,282, filed on Oct. 5, 2006.

(51) Int. Cl.
*G08B 1/08* (2006.01)
*G09F 1/10* (2006.01)
*G09F 3/10* (2006.01)

(52) U.S. Cl. ............ 340/539.13; 340/539.12; 40/124.06; 40/299.01

(58) Field of Classification Search ... 340/539.1–539.2, 340/573.1, 571, 572.1–572.9, 505, 3.1, 825.36; 40/124.01–124.08, 299.01, 625–633, 5
See application file for complete search history.

(56) References Cited

U.S. PATENT DOCUMENTS

4,068,213 A * 1/1978 Nakamura et al. .......... 235/381

(Continued)

FOREIGN PATENT DOCUMENTS

WO    WO/2005/046433    5/2005

OTHER PUBLICATIONS

Lenert, L. et al.; An Intelligent 802.11Triage Tag for Medical Response to Disasters; AMIA 2005 Symposium Proceedings; pp. 440-444.

(Continued)

*Primary Examiner*—Jennifer Mehmood
(74) *Attorney, Agent, or Firm*—Francis A. Cooch

(57) ABSTRACT

The present disclosure is directed towards apparatuses, systems and methods for providing improved sensor-based patient monitoring and tracking. In accordance with one aspect, a method is provided for adjusting a vital sign alarm threshold of a vital status sensor as a function of a patient's GPS data, which may comprise: altitude data, velocity data, and position data. In accordance with another aspect, a method is provided for adjusting one or more alarm detection parameters based in part on a patient's calculated heart rate variability (HRV) data. According to yet another aspect, an electronic triage tag is configured to include a colored card insertion region for inserting a colored card for preventing the device from being inadvertently activated, an LCD screen and a series of LEDs for displaying the triage status of a patient (red, yellow, green, black).

3 Claims, 6 Drawing Sheets

U.S. PATENT DOCUMENTS

| | | |
|---|---|---|
| 5,515,440 A * | 5/1996 | Mooney et al. ............. 713/159 |
| 5,771,001 A | 6/1998 | Cobb |
| 6,198,394 B1 * | 3/2001 | Jacobsen et al. ......... 340/573.1 |
| 6,293,861 B1 | 9/2001 | Berry |
| 7,123,137 B2 | 10/2006 | Heck et al. |
| 7,304,578 B1 * | 12/2007 | Sayers et al. ............. 340/572.3 |
| 2002/0011518 A1 | 1/2002 | Goetz et al. |
| 2004/0158740 A1 * | 8/2004 | Lien et al. ................... 713/200 |
| 2005/0071190 A1 | 3/2005 | Herger et al. |
| 2006/0000296 A1 * | 1/2006 | Salter ..................... 73/863.01 |
| 2006/0142648 A1 | 6/2006 | Banet |
| 2006/0206011 A1 | 9/2006 | Higgins et al. |
| 2006/0261958 A1 | 11/2006 | Klein |

OTHER PUBLICATIONS

Lenert, L. et all; UCSD Tests Intelligent Triage, Other Technologies in San Diego Disaster Drill; Nov. 21, 2005 issue of UCSD jacobs School of Engineering; pp. 1-10.

Miami Medical; Vita Sign Monitors,www.Miami-med.com/pulseoxihtm; pp. 1-4.

Cooke et al.; Heart Rate Variability and It's Association with Mortality in Prehospital Trauma Patients: The Journal of Trauma, Injury . . . Feb. 2006, vol. 60(2) pp. 363-370 pgs.

* cited by examiner

SENSOR-BASED ADAPTIVE WEARABLE DEVICES AND METHODS

CROSS REFERENCE TO RELATED APPLICATIONS

This application claims the benefit of prior filed, U.S. provisional applications: Ser. No. 60/795,815, filed on Apr. 28, 2006; Ser. No. 60/849,570, filed on Oct. 5, 2006; and Ser. No. 60/828,282, filed on Oct. 5, 2006.

STATEMENT OF GOVERNMENTAL INTEREST

This invention was made with Government support under National Library of Medicine contract N01-LM-3-3516. The Government has certain rights in the invention.

BACKGROUND OF THE INVENTION

1. Field of the Invention

The present invention relates generally to patient monitoring and, more particularly, to systems, methods and apparatus for improved patient monitoring utilizing sensor-based adaptive wearable devices.

2. Description of the Related Art

During a mass emergency, many injured people must be helped in a quick and efficient manner. A clever triage system proficiently chooses the order in which individuals are sent to the hospital. A valuable triage also defines an effective system that distributes limited medical resources in a manner that helps as many people as possible. At a disaster scene, it is critical that patients are correctly diagnosed, monitored, and located to ensure the preservation of the maximum number of lives. Unfortunately, the current systems use paper triage tags that inefficiently monitor and locate patients during mass casualty situations.

In a mass casualty situation, the rapid and accurate triage (counting and sorting) of patients is the critical early step in the emergency response process. As noted above, the paper triage tags currently in use by EMS groups, however, are far from efficient. In the paper triage tag system, a first responder attaches a paper tag or colored ribbon to each patient. The first responder then calls the triage officer and reports the patient count. The commander tallies the patient numbers and calls for the necessary number of ambulances. Paper tags employ color codes to determine the severity of the patient's injury. Patients classified as red are considered to need the most immediate attention, followed by patients classified as yellow. Patients classified as green are the least severely injured and patients classified as black are deceased or expectant. After completing initial triage, patients wait at the scene until their designated ambulance arrives. With a resource limited response team, patients often wait for an extended period of time before transport. During this waiting period, patient conditions may deteriorate.

The paper-tag based triage process has many limitations. These include, the wasting of critical time between the time a patient is triaged and the time that information is received by the triage officer, human counting error in counting and tallying triaged patients, the possibility of misuse of paper tags by patients who retriage themselves to a higher priority level, limited visual feedback from the tags at a distance, tags that do not aid in locating a particular patient in a mass of patients, tags that do not distinguish between patients categorized under the same color. Other notable limitations include, categorizing two patients as critical (red) when their respective vital signs designate one to be much worse than the other, no obvious visual differentiation of contaminated versus uncontaminated patients, the inability of responders to track patients who leave the scene without authorization, the non-detection of a lapsed or out of date patient triage status when a patient deteriorates and illegible information on paper tags as a consequence of recording information under time pressure.

The afore-mentioned drawbacks associated with paper tags are overcome by electronic triage tags, sometimes referred to as E-tags. It is noted, however, that while electronic tags overcome the afore-mentioned drawbacks associated with paper tags, they introduce other unique drawbacks. For example, an electronic tag does not show any color coding information when the battery runs out. An electronic tag may be misused by patients who attempt to set their own triage color via the push of a button and the LEDS used with such tags have limited visibility in sunlight. A novel electronic tag of the invention overcomes these and other drawbacks, as will be described below.

While an electronic tag is well suited to mass casualty situations by greatly benefiting a host of patients at a disaster scene by providing patient location and status information, on a mass scale, to medical personnel, its role may be expanded via the integration of vital sign sensors to provide continuous monitoring of a patient's vital signs until they are admitted to a hospital. By integrating vital sign sensors within the electronic tag, medical personnel are provided with a means for simultaneously tracking the vital signs of a large number of patients in an efficient manner. Furthermore, it gives the medical personnel immediate notification of any changes in patient status, such as respiratory failure or cardiac arrest.

One vital sign sensor which has been contemplated for use within an electronic tag is an arrhythmia monitor for detecting patient arrhythmias. As is well known, an arrhythmia monitor provides heart rhythm data, which is supplied to the electronic tag for transmission to a central station for patient monitoring by medical personnel. The applicant has recognized that while the ability to track a patient's heart rhythms and transmit the data in real-time to medical personnel on a mass scale is useful, its usefulness may be enhanced by considering measurements, outside of those conventional measurements to trigger alarms. Specifically, vital sign sensors in present day use typically track a patient's heart rhythms using a set of standard measurements, including, oxygen saturation, pulse pressure and heart rate. While these measurements are very useful in tracking a patient's heart rhythms, the applicant has recognized that certain unconventional measurements, not heretofore considered in the art, may improve the accuracy of automated vital signs monitoring to provide a more accurate picture of a patient's health. Specifically, the applicant has recognized two unconventional measurements that may be useful in providing a more accurate picture of a patient's health. One measurement is a patient's altitude reading (height above sea level). The applicant has recognized that altitude is an important, yet overlooked, parameter in monitoring a patient's heart rhythms, in that it is well known that altitude affects heart rate and blood oxygen concentration and therefore should be considered as a factor in detecting patient arrhythmias. The present invention addresses this limitation by providing a method for dynamically adjusting a patient alarm threshold in a vital sign sensor, such as an arrhythmia monitor, based on a patient's altitude data.

The second unconventional measurement that may prove useful in providing a more accurate picture of a patient's health is a patient's heart rate variability (HRV) reading. It has been shown that patients have a higher survival rate who exhibit HRV values, expressed as HF/LF ratios, of 64+/−12, while terminal patients exhibit HF/LF ratios of 172+/−32. Accordingly, this HRV information may be utilized to adjust an alarm detection parameter of the heart rate monitor sensor to provide a more accurate assessment of a patient's physical condition.

SUMMARY OF THE INVENTION

Therefore, the present invention has been made in view of the above problems, and it is an objective of the present invention to provide methods and systems for providing improved sensor-based patient monitoring and tracking.

In accordance with one aspect of the present invention, the afore-mentioned objective is achieved by providing a method for adjusting a vital sign alarm threshold of a vital status sensor as a function of a patient's GPS data, which may comprise, in certain embodiments, altitude data, velocity data, and position data. The method generally comprises: periodically receiving patient GPS data; and adjusting at least one patient vital sign alarm threshold based on the received patient GPS data.

In accordance with another aspect of the present invention, the afore-mentioned objective is achieved by providing a program product for adjusting a vital sign alarm threshold of a vital status sensor as a function of a patient's altitude. The computer program product includes executable code for performing a method comprising: periodically receiving patient GPS data; and adjusting at least one patient vital sign alarm threshold based on the received patient GPS data.

In accordance with another aspect of the present invention, the afore-mentioned objective is achieved by providing a method for adjusting an alarm detection parameter based on a patient's calculated heart rate variability (HRV) data. The method generally comprises: periodically receiving patient heart rate data, converting the patient heart rate data to HRV data; and adjusting at least one patient alarm detection parameter based on the HRV data.

In accordance with another aspect of the present invention, the afore-mentioned objective is achieved by providing a computer program product for adjusting an alarm detection parameter of a patient vital status sensor as a function of heart rate variability (HRV) data. The computer program product includes executable code for performing a method comprising: periodically receiving heart rate data; converting the received heart rate data to HRV data and adjusting at least one patient alarm detection parameter based on the HRV data.

In accordance with another aspect of the present invention, the afore-mentioned objective is achieved by providing a system for providing real-time patient monitoring and tracking in emergency situations. The system comprises wearable computers including vital sign and location sensors, ad-hoc networking, a database and web portal technology to allow computer monitoring of patient status in real-time.

According to one or more aspects, an electronic triage tag may be configured to: include (i) vital sign monitoring functions, (ii) location tracking functions; (iii) alarm signaling functions; (iv) information display functions, (v) receive a patient's triage status, (vi) display the received patient triage status (vii) initiate a communication session, (ix) establish a communication link to communicate patient vital sign data, patient triage status, and patient location information.

As will be apparent, the present invention may generally benefit patients in emergency settings and other outdoor situations by providing improved vital signs monitoring to provide a more accurate picture of a patient's health. More particularly, it will be appreciated that the improved monitoring techniques disclosed herein will provide medical personnel with the ability to take pre-emptive action before a patient's condition degrades severely.

BRIEF DESCRIPTION OF THE DRAWINGS

These and other objects, features and advantages of the invention will be apparent from a consideration of the following Detailed Description Of The Invention considered in conjunction with the drawing Figures, in which.

DETAILED DESCRIPTION

Figure 1:
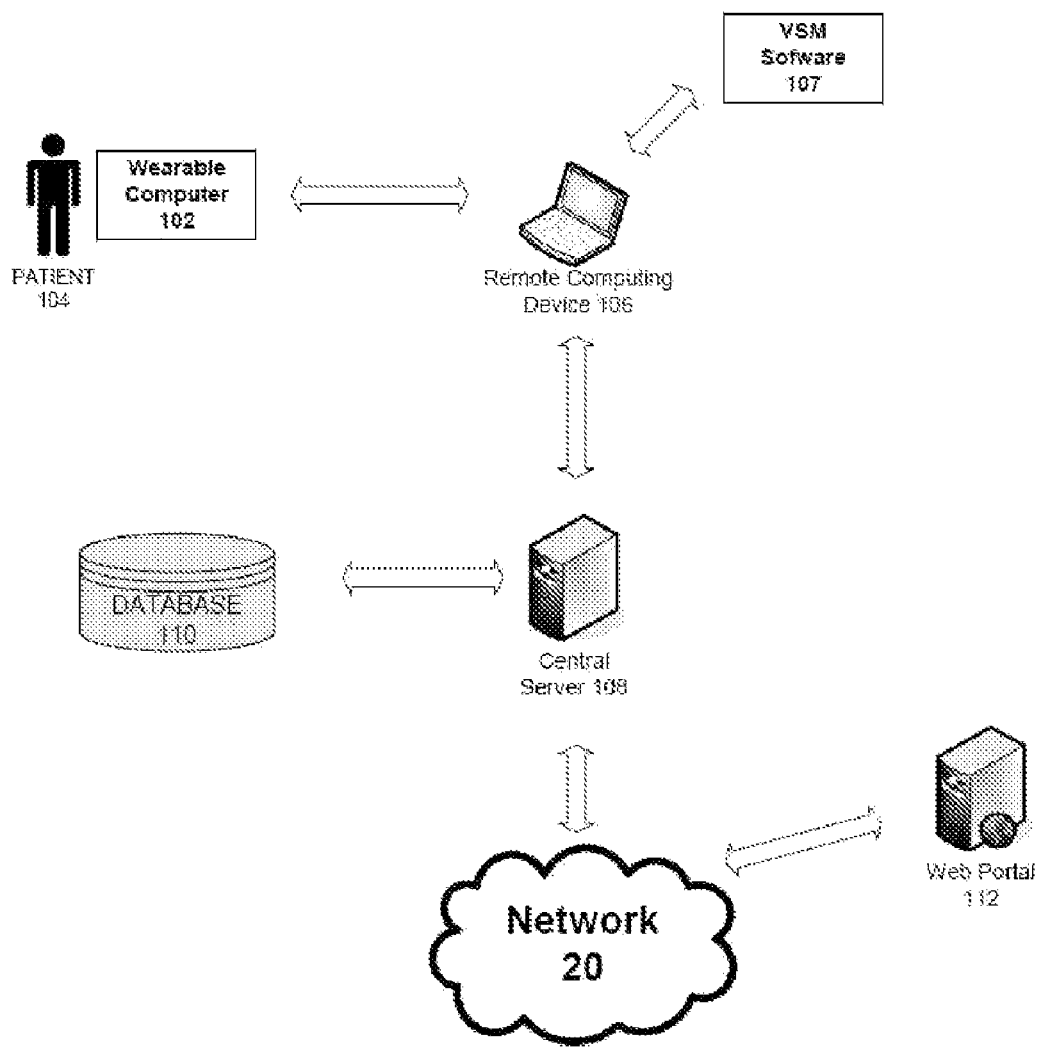
FIG. 1 is a block diagram of a real-time patient monitoring and tracking system, in accordance with one embodiment.

With reference now to FIG. 1, there is shown one embodiment of a real-time patient monitoring and tracking system 100 to continuously monitor a plurality of patient's vital status and track their locations until they are admitted to a hospital.

The real-time patient monitoring and tracking system 100 is seen to comprise, in the exemplary embodiment, a wearable computer 102, preferably attached to the wrist of a patient 104, a remote computing device 106 for receiving patient information (i.e., vitals) from the wearable computer 102. Communications between the wearable computer 102 and the computing device 106 is performed wirelessly. In an embodiment, the wireless communication may be performed in accordance with the IEEE 802.15.4 communication standard. Of course, other standards, that exist or become known, are contemplated for use with the invention. The computing device 106 requires a network connection to communicate with a central server 108. In one embodiment, the network connection may use, for example, Verizon's EVDO coverage by inserting an EVDO wireless card in the remote computing device 106.

The real-time patient monitoring and tracking system 100 further comprises a web portal 112 to connect with a database 110 and make the real-time information accessible to users from Internet browsers. The web portal 112 will be used by different participants in the emergency response team, such as the emergency department personnel who need this information to prepare for the incoming patient. The database 110 is connected to the web portal 112 through the use of well defined web services. Patient information is transmitted over SOAP, a secure and encrypted form of XML. The web service based approach advantageously provides flexibility to interoperate with third-party software in the future.

Wearable Computer

Figure 2:
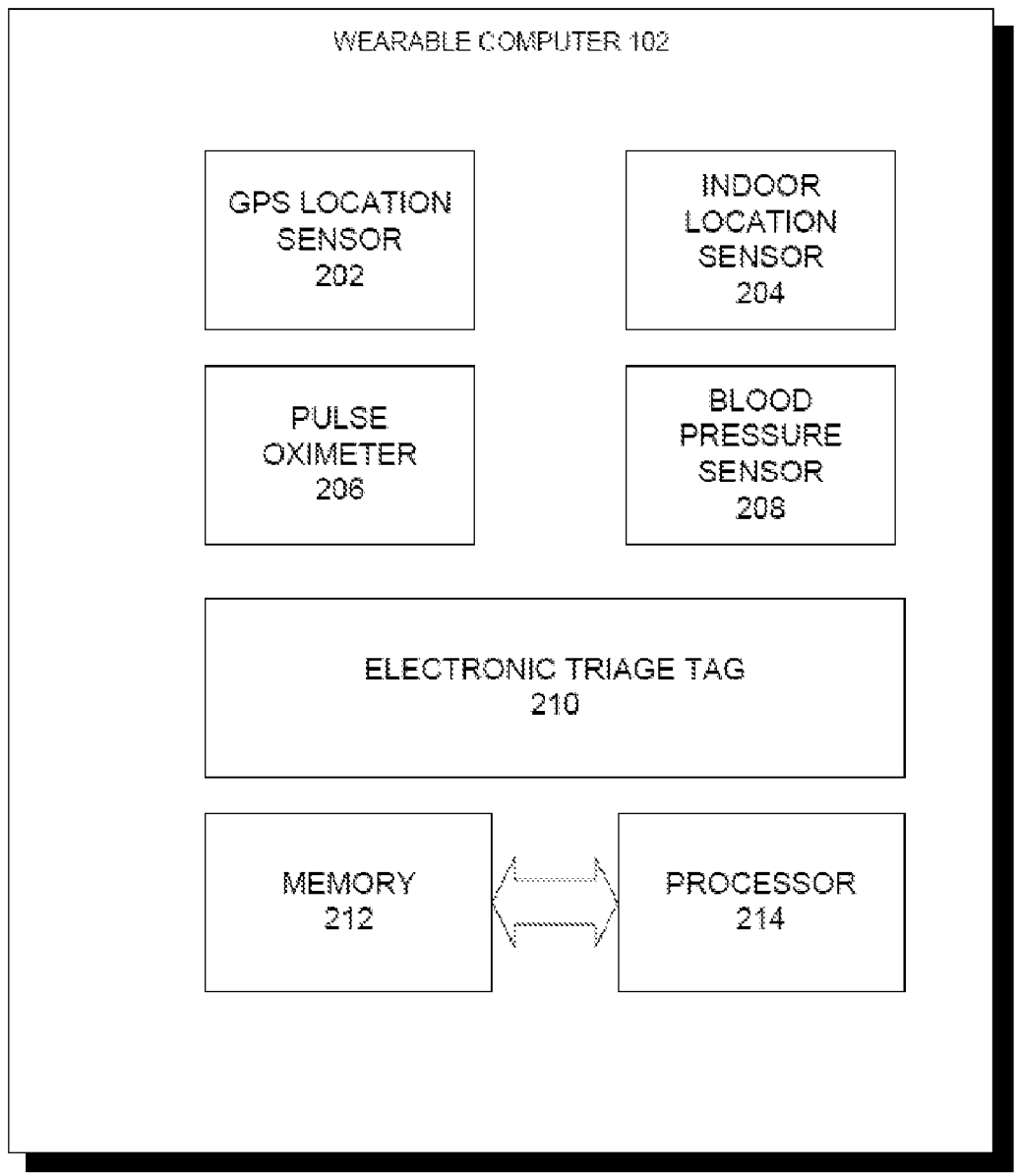
FIG. 2 illustrates the wearable computer of FIG. 1, according to one embodiment.

Turning now to FIG. 2, there is shown a more detailed illustration of the wearable computer computer 102 that is seen to comprise, a memory 212 coupled to a processor 214 and several peripheral devices, including, according to one embodiment, a GPS location sensor 202 for outdoor use, an indoor location sensor 204 for indoor use, a wearable pulse-oximeter 206, a blood pressure sensor 208, and an electronic triage tag 210. The processor 214 may be or include any type, quantity, and/or configuration of processor that is or becomes known. In some embodiments, the processor 214 may comprise multiple inter-connected processors, microprocessors, and/or micro-engines. The processor 214 may be in communication with and/or coupled to any number of other components of the wearable computer 102 such as the GPS location sensor 202, the blood pressure sensor 208, the electronic triage tag 210, and the memory 214.

The electronic triage tag 210 is a portable status-relaying apparatus configured to allow medical personnel to set the triage color (red/yellow/green) of the patient by inserting a color coded card, as will be described further below. The electronic triage tag 210 replaces the paper triage tags that are commonly used by medics today.

The pulse oximeter 206 attaches to the patient's finger and measures patient heart rate (HR) and blood oxygenation level ($SpO_2$). A cuff pressure sensor on the patient's upper arm measures systolic and diastolic blood pressure.

The GPS location sensor 202 provides geo-location and allows medics to track patients who are outdoors, e.g., at the scene of the emergency, to within an accuracy of 3 meters (CEP). The indoor location sensor 204 provides location information for those places where the GPS location sensor 202 cannot be reached and requires the installation of location beacons.

In an embodiment, the wearable computer 102 provides four primary functionalities: vital sign monitoring, location tracking, medical record storage, and triage status tracking.

System Operation

With reference now to FIGS. 1 and 2, the system operation will be described. With all of the peripheral devices of wearable computer 102 turned on, the pulse oximeter 206 wirelessly reports patient data, via the electronic triage tag 210, to the remote computing device 102, every second. The GPS location sensor 202 wirelessly reports to the computing device 102, via the electronic triage tag 210, every 5 minutes. The blood pressure sensor 208 reports to the computing device 102 every 15 minutes. It is noted that the battery lifetime of the overall system is approximately 6 hours, however, when the blood pressure sensor 208 is not in use, the battery lifetime can be extended to 1-2 days.

Vital Sign Monitor Algorithm

A software application on the computing device 106 (see FIG. 1), referred to as a Vital Sign Monitor (VSM), receives real-time patient data from the wearable computer 102, and processes the patient data to detect anomalies. The VSM software application 107 includes a GUI (not shown) to review the patient data (e.g., real-time ECG, $O_2$ saturation level, and heart rate of each patient), as well as any alarms. When any of the vital signs surpass preset thresholds, which are also manually adjustable, an appropriate alert pops up to notify the nurse or physician in charge.

The following table shows a partial list of physiological conditions that may cause an alert in the VSM software application 107 on the computing device 106.

TABLE I

ALERT DETECTION PARAMETERS

| | Alert Type | Detection Parameter |
|---|---|---|
| 1. | Low $SpO_2$ | $SpO_2 < 90\%$ |
| 2. | bradycardia | HR < 40 bpm |
| 3. | tachycardia | HR > 150 bpm |
| 4. | HR change | $|\Delta$ HR/5 min $|$ > 19% |
| 5. | HR stability | max HR variability from past 4 readings |
| 6. | BP change | systolic or diastolic change > ±11% |

The VSM software application 107, running on the computing device 106, is integrated with a database 110. The computing device 106 regularly transmits patient data (vital signs, location, triage color) and alerts for multiple patients to the database 110 via a wireless network 20. If network connectivity is unavailable, the VSM software application 107 running on the computing device 106 continues to operate.

When an anomaly is detected in the patient vital signs (e.g., see Table I), the VSM software application 107 generates an alert in the computing device user interface (GUI). The medic can locate the patient by selecting to view a map of the disaster scene marked with the GPS location of each patient. The medic can also select a "sound alert" feature that will sound a buzzer and blink an LED on the wearable computer 102.

Web Portal

The system 100 supports the need for multiple parties to share information about patient's status and locations. A Web based information portal 112 allows different types of users to access the patient information in real-time. When a user logs in to the web portal 112, the information displayed to the user is managed by group-level permissions. In one embodiment, the Web portal 112 contemplates three levels of users: emergency department personnel who log in to the web portal 112 to retrieve information about the patients who are being transported to their hospital, incident commanders who login to the web portal 112 to see summaries of patients at particular disaster scenes and medical specialists, often located at distant facilities, who may be called on to give treatment instructions to the medics at the scene.

According to one embodiment of the present invention, a method is disclosed for dynamically adjusting one or more alarm detection parameters in accordance with dynamically received heart rate variability (HRV) data, in which the HRV data is derived from a patient's heart rate data. In this manner, improved vital signs monitoring is realized which provides a more accurate picture of a patient's health. The alarm detection parameters are adjusted in the context of a process for detecting heart arrhythmias in a patient (e.g., Asystole, Bradycardia and VT).

As is well known to those in the medical arts, Asystole is a condition in which the heart stops beating, Bradycardia is where the heart experiences a number of consecutive slow beats (i.e., a slow pulse rate), and VT is where the heart experiences a number of consecutive beats above a threshold rate with low $O_2$ or unstable $O_2$.

As is also well known to those knowledgeable in the medical arts, heart rate variability (HRV) is generally defined as the beat-to-beat variance in heart rate exhibited in the human cardiopulmonary system and may be expressed in one way as a ratio of high frequency heart rate data to low frequency heart rate data, i.e., HF/LF.

The method for dynamically adjusting one or more alarm detection parameters in accordance with dynamically received heart rate variability (HRV) data, according to the present embodiment, is premised on a scientifically proven result that patients who exhibit HRV numbers, expressed as an HF/LF ratio of 64+/−12 have a higher survival rate, while patients who exhibit HF/LF ratios of 172+/−32 are considered to be terminal. Accordingly, the patient HRV data may be advantageously utilized to provide a more accurate assessment of a patient's physical condition.

Figure 3:
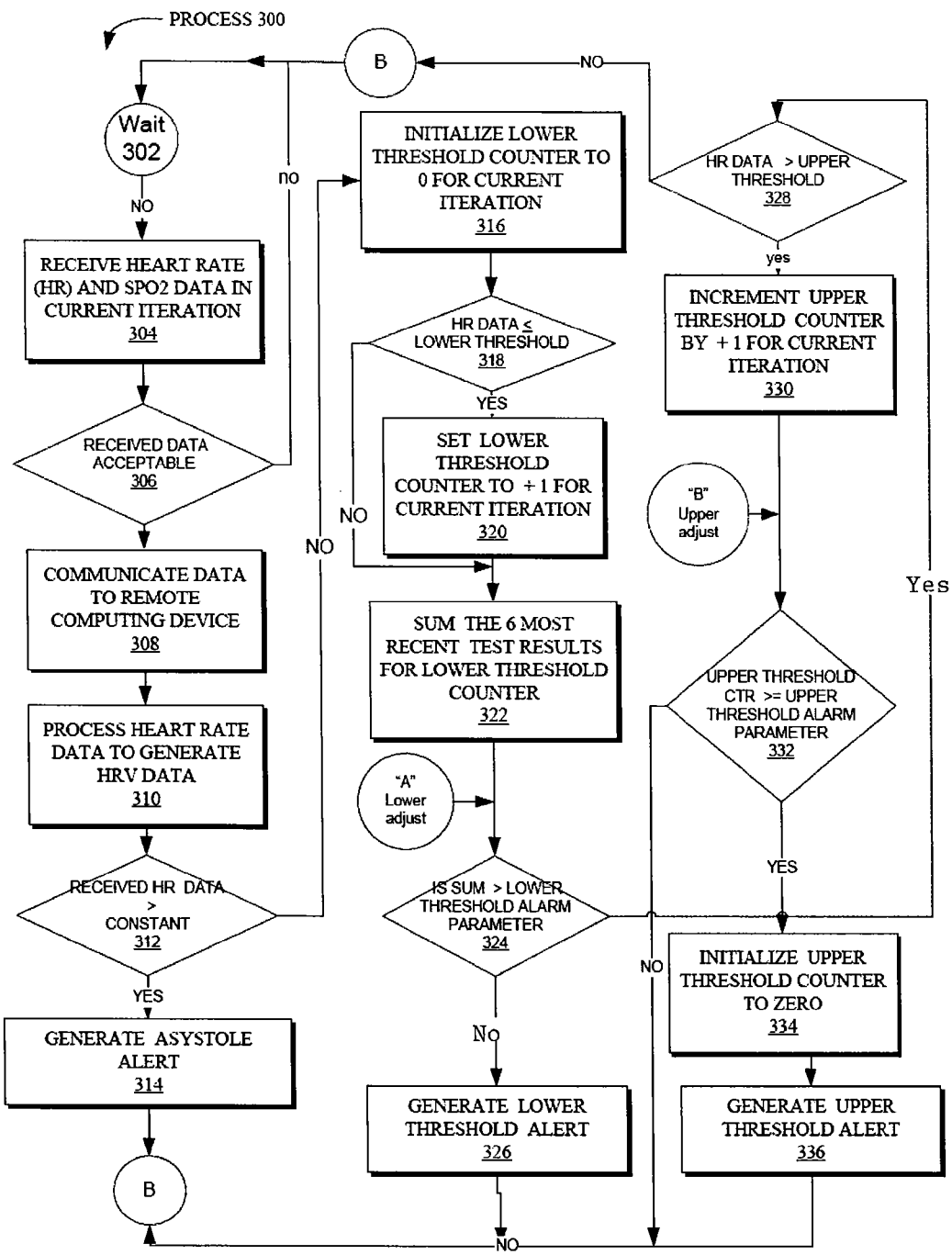
FIG. 3 illustrates a method for dynamically adjusting one or more alarm detection parameters as a function of patient HRV data, in accordance with a process flow for detecting of various types of heart arrhythmias in patients, according to one embodiment.

With reference now to FIG. 3, there is described a method for dynamically adjusting one or more alarm detection parameters, according to received patient HRV data, in the context of a process flow 300 for detecting various types of heart arrhythmias in patients (e.g., Asystole, bradycardia and Ventricular tachycardia (VT)).

The electronic triage tag 210 for a particular patient 104 resides in a wait mode until it receives patient data comprising heart rate data and SpO$_2$ data (302). Heart rate and SpO$_2$ data is received from sensors on the electronic triage tag 210, for the current iteration (304). A determination is then made regarding whether the received heart rate and SpO$_2$ data is acceptable based on a threshold criteria (306). If the data is determined to be unacceptable, the process returns to the wait state 302. Otherwise, if the data is determined to be acceptable, the heart rate and SpO$_2$ data are communicated from the patient's wearable computer 102 to the remote computing device 106 to be processed by the vital sign monitoring (VSM) software application 107, running on the computing device 106 (308). The heart rate data received from the patient's wearable computer 102 is processed by a power spectrum algorithm running on the computing device 106 to generate HRV data (310). The conversion process from patient heart data to HRV data is described in greater detail further below.

A determination is then made regarding whether the heart rate (HR) data for the current iteration is greater than a pre-determined constant specifying a time interval (bpm) which when exceeded triggers an asystole alarm (312). If the heart rate (HR) data is determined to be greater than the predetermined constant, an asystole alarm is generated and the process returns to 302 (314). Otherwise, if the heart rate (HR) data, received in the current iteration, is determined to be less than the predetermined constant, a lower threshold counter is initialized to zero for the current iteration (316). A determination is then made regarding whether the heart rate (HR) data, received in the current iteration, is less than or equal to a pre-defined lower threshold (318) (e.g., 40 bpm). If the determination is not true, the process continues at 322. Otherwise, a lower threshold counter is incremented by +1 for the current iteration (320). Next, the lower threshold counter is summed for the six most recent test iterations (322). A determination is then made regarding whether the summation is greater than the lower threshold alarm parameter (324). If the determination is true, the process continues at 328, otherwise, a lower threshold alert is generated and the process returns to the wait state at 302 (326). A determination is then made regarding whether the heart rate (HR) data, received in the current iteration, is greater than a pre-determined upper threshold, (e.g., 165 bpm) (328). If the determination is not true, the process returns to the wait state at 302. Otherwise, an upper threshold counter is incremented by +1 for the current iteration (330). A determination is then made regarding whether the updated upper threshold counter is greater than an upper threshold alarm parameter (332). If the determination is not true, the process returns to the wait state (302), otherwise, the upper threshold counter is initialized to zero (334) and an upper threshold alert is generated (336) and the process returns to the wait state at 302.

It should be appreciated that a key feature of the process flow illustrated in FIG. 3, is the modification (adjustment) of the upper and lower threshold alarm parameters, in accordance with HRV data, derived from heart rate data, received in the current iteration. More particularly, the lower and upper alarm detection parameters are modified (adjusted) in connection with determinations steps 324 and 332 of FIG. 3, see "A" and "B" respectively. It should be noted that by dynamically adjusting the upper and lower alarm detection parameters, in accordance with HRV data, improved vital signs monitoring is achieved which provides a more accurate picture of a patient's health. Moreover, medical personnel are provided with the ability to take pre-emptive action before a patient's condition degrades severely.

Converting Heart Rate Data to HRV Data

Instantaneous heart rate is determined by the power spectrum algorithm using the time interval between R-wave complexes in ECGs, known as RR intervals. Sensor input data from a medical sensor (e.g., ECG, Pulse Oximeter) is interpolated and re-sampled at over 0.8 Hz, depending on the original sampling frequency. A fast Fourier Transform (FFT) is performed to provide a frequency domain array corresponding to different frequency bands determined by the sampling rate. The interval between elements of the array is the sampling frequency (Hz) divided by n, the number of elements fed into the FFT method. The data is sent to a low-pass filter at 0.4 Hz to remove the erroneous frequencies which do not factor into the analysis of HRV. The isolated elements of the array are broken down into LF (0.05 to 0.15 Hz) and HF (0.15 to 0.4 Hz). It was found that patients who survived, exhibited HF/LF ratios of 64±12, while terminal patients exhibited ratios of 172±32.

In some embodiments, the heart rate data may be processed in other ways to generate HRV data. For example, in an embodiment, it is contemplated that the heart rate data may be processed to create a multiplicity of segments in the frequency domain rather than the two segments previously described above, i.e., a high (HF) segment and a low (LF) frequency segment from which the HRV data may be generated.

In accordance with another embodiment of the present invention, periodically received GPS information is used to dynamically adjust lower and upper threshold values associated with a patient arrhythmia detection algorithm, embodied as a software program in a remote computing device. The GPS information may comprise different types of information, including, but not limited to, altitude data for improving the detection accuracy of a potential patient arrhythmia over traditional methods. The inventor has recognized that altitude levels affect heart rate and blood oxygen concentration. Therefore, improved detection accuracy may be realized by considering patient altitude data in the patient arrhythmia detection algorithm.

The arrhythmia detection algorithm, incorporating certain invention principles specific to the present embodiment, is preferably executed as a software application (i.e., VSM software 107 as shown in FIG. 1) in the remote computing device 106. The detection algorithm is configured to analyze data resulting from the non-invasive monitoring of a patient's heart rate and oxygenation level via the pulse oximeter 208, which is a sensor on the wearable computer 102 (see FIGS. 1 and 2).

The detection algorithm, according to the presently described embodiment, dynamically adjusts one or more vital sign alarm thresholds according to received altitude data (received as remote GPS data). In this manner, improved arrhythmia detection accuracy may be achieved over more traditional non-adaptive algorithms.

It is noted that the present embodiment differs from the previously described embodiment in that adjustments are made to one or more alarm detection parameters in the previous embodiment, according to HRV data, while the present embodiment adjusts one or more alarm thresholds in accordance with GPS data.

Figure 4:
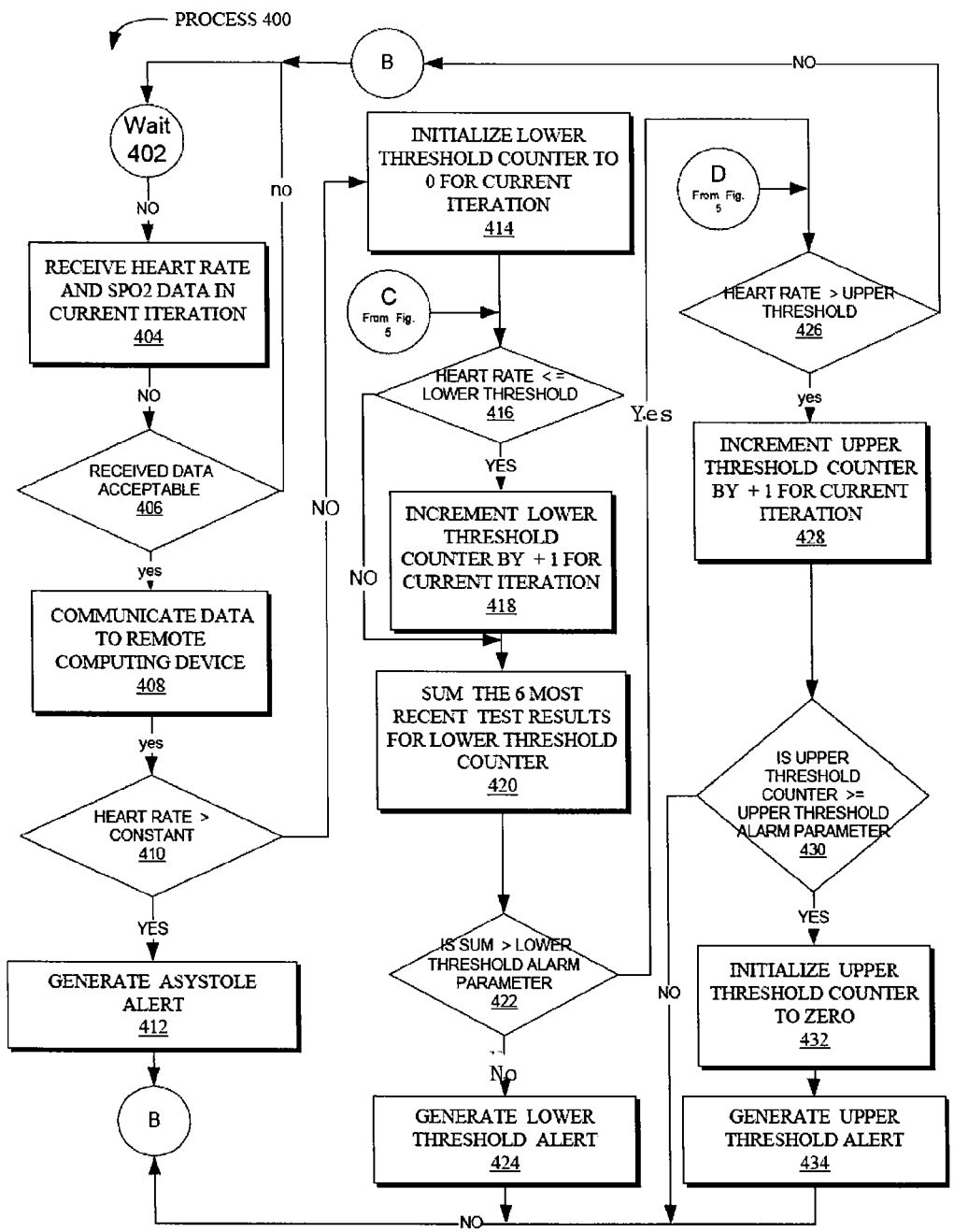
FIG. 4 illustrates a method for dynamically adjusting one or more alarm detection thresholds as a function of remotely received GPS data, in accordance with a process flow for detecting of various types of heart arrhythmias in patients, according to one embodiment.

With reference now to FIG. 4, there is illustrated a method for dynamically adjusting one or more alarm detection thresholds in accordance with remotely received GPS data. The method is performed in accordance with a process flow 400 for detecting various types of heart arrhythmias in patients.

The process flow 400 begins with the electronic triage tag 210 operating in a "wait" mode to receive heart rate data and $SpO_2$ data (402) from sensors 206, 208 on the tag 210. Upon receiving data for a current iteration, (404), a determination is then made regarding whether the received heart rate and $SpO_2$ data is acceptable based on some data threshold criteria (406). If the data is determined to be unacceptable, the process returns to the "wait" mode (402), otherwise, the data is wirelessly communicated to a remote computing device 106 (408) to be processed by the VSM software 107 (See FIG. 1). The VSM software 107 processes the received data by first making a determination regarding whether the received heart rate data for the current iteration is greater than a predetermined constant, i.e., a heart rate time interval, in units of beats per minute (bpm) (410). If the predetermined constant (threshold) is exceeded, an asystole alarm is triggered (412) and the process returns to the wait state 402. Otherwise, if the predetermined constant (threshold) is not exceeded, a lower threshold counter is initialized to zero for the current iteration (414). A determination is then made regarding whether the received heart rate data for the current iteration is less than or equal to a heart rate lower threshold, which can be set to, for example, 40 bpm (416). If the heart rate (HR) data, received in the current iteration, is determined to be less than or equal to the lower threshold, a lower threshold counter is incremented by +1 for the current iteration (418). Otherwise, the lower threshold counter remains unchanged in the current iteration. Next, the lower threshold counter is summed for the six most recent iterations (420). Then, a determination is made regarding whether the summation is greater than a lower threshold alarm parameter (422). If it is determined that the summation is not greater than the lower threshold alarm parameter, a lower threshold alert is generated and the process returns to the wait state 402 (424). Otherwise, if it is determined that the summation is greater than the lower threshold alarm parameter, a determination is made regarding whether the heart rate (HR) data received in the current iteration, is greater than a pre-determined upper threshold, which can be set to, for example, 165 bpm (426). If this determination is true, the upper threshold counter is incremented by +1 for the current iteration (428). If this determination is not true, the process returns to the wait state at 402. If the determination is true, a determination is then made regarding whether the upper threshold counter is greater than or equal to the upper threshold alarm parameter (430). If this determination is not true, the process returns to the wait state at 402, otherwise, the upper threshold counter is initialized to zero (432) and an upper threshold alert is generated (434).

Figure 5:
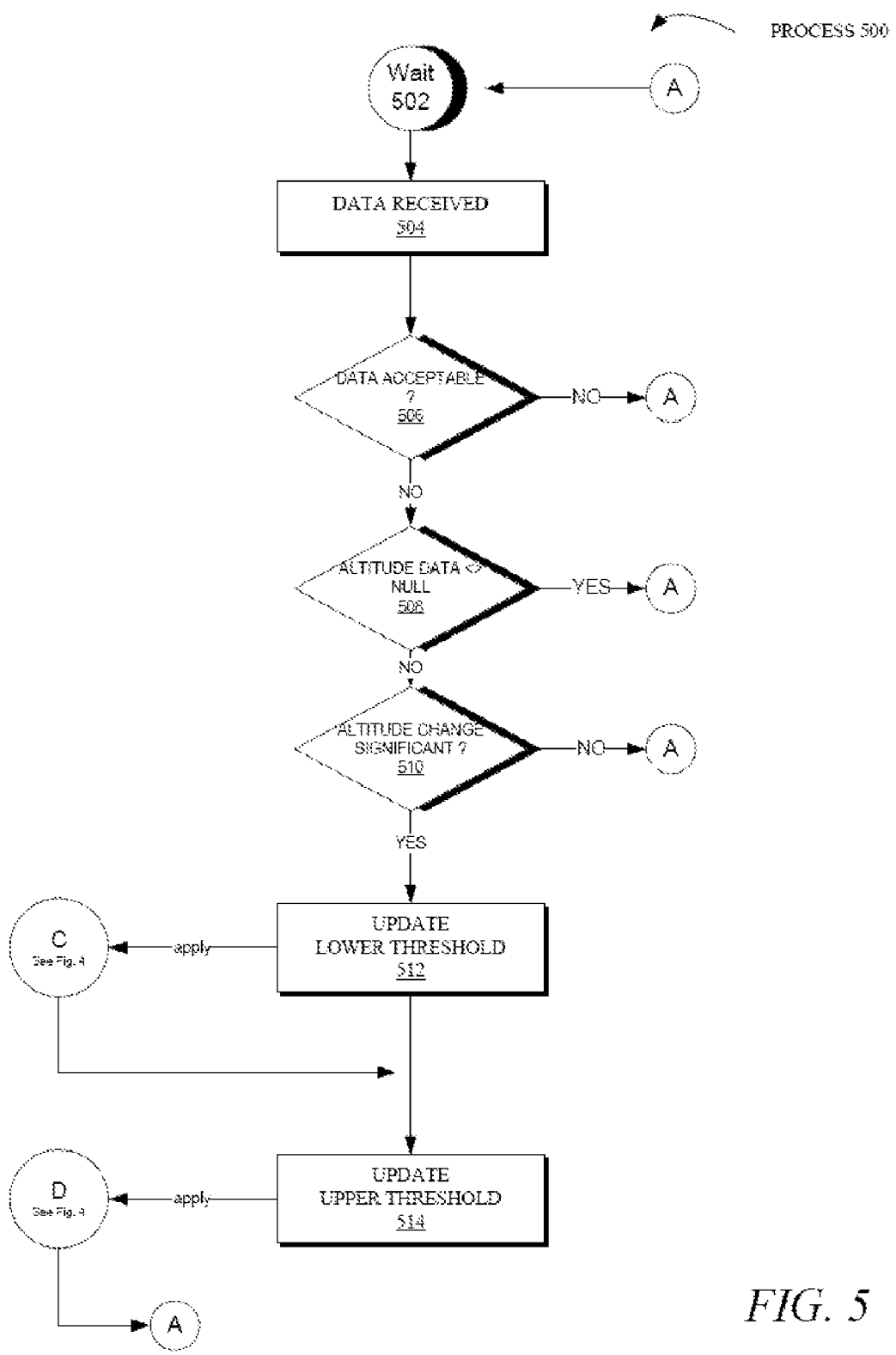
FIG. 5 illustrates a process for processing the remotely received GPS data in accordance with the process flow of FIG. 4, according to one embodiment.

It should be appreciated that a key feature of the process flow illustrated in FIG. 4, is the modification of the upper and lower alarm thresholds, in accordance with received GPS data (See FIG. 5). More particularly, the lower and upper alarm thresholds are preferably modified in accordance with remotely received GPS, as shown in the process flow of FIG. 4 in association with decision steps 422 and 430, see labels "C" and "D" respectively. By dynamically adjusting the upper and lower alarm thresholds according to remotely received GPS data (e.g, patient altitude data), improved vital signs monitoring is achieved which provides a more accurate picture of a patient's health. Moreover, medical personnel are provided with the ability to take pre-emptive action before a patient's condition degrades severely.

With reference now to FIG. 5, there is described a process 500 for processing the GPS data (e.g., altitude readings) to determine whether or not to dynamically adjust the lower and upper threshold values at steps 414 and 424 of the process flow illustrated in FIG. 4 for detecting heart arrhythmias. The GPS data is preferably received via a GPS receiver (not shown) on the wearable computer 102.

The electronic triage tag 210 on the wearable computer 102 for a particular patient 104 resides in a wait mode until it receives a GPS altitude reading (502). Heart rate and $SpO_2$ data is received from sensors on the electronic triage tag 210, for the current iteration (504). Upon receiving the GPS altitude data, a determination is made regarding whether the GPS altitude data is acceptable based on some pre-determined threshold criteria (506). If the data is considered acceptable, the process continues at 508, otherwise, the process returns to 502 to wait for the next data transmission. A determination is made regarding whether the GPS data corresponding to the patient's current altitude is NULL data (508). If it is determined that the data is NULL data, the process returns to 502 to wait for the next data transmission of heart rate and $SpO_2$ data. Otherwise a determination is made regarding whether the GPS data corresponding to the patient's altitude is significantly changed from the most recently received data (510). If the change is determined to be insignificant, the process returns to wait for the next data transmission of heart rate and $SpO_2$ data at 502. Otherwise, a lower alarm threshold for detecting patient heart arrhythmias is adjusted, in accordance with a detected change in the patient GPS data corresponding to the patient's currently reported altitude (512). For example, if the changed data is determined to be a positive change in altitude, the lower threshold alarm parameter is adjusted upward to account for the patient's increased oxygen demand at an increased altitude. Conversely, if the changed GPS data is determined to be negative, the lower alarm threshold is adjusted downward to account for the patient's decreased oxygen demand at a decreased altitude. The adjustment of the lower alarm threshold is performed just prior to the decision diamond at 416 in the flowchart of FIG. 4, see label "C". An upper alarm threshold for detecting patient heart arrhythmias is adjusted, in accordance with a detected change in the patient GPS data corresponding to the patient's currently reported altitude (514). For example, if the changed data is determined to be a positive change in altitude, the upper threshold alarm parameter is adjusted upward to account for the patient's increased oxygen demand at an increased altitude. Conversely, if the changed GPS data is determined to be negative, the upper threshold alarm parameter is adjusted downward to account for the patient's decreased oxygen demand at a decreased altitude. The adjustment of the upper alarm threshold is performed just prior to decision diamond 426 in the flowchart of FIG. 4, see label "D".

Figure 6:
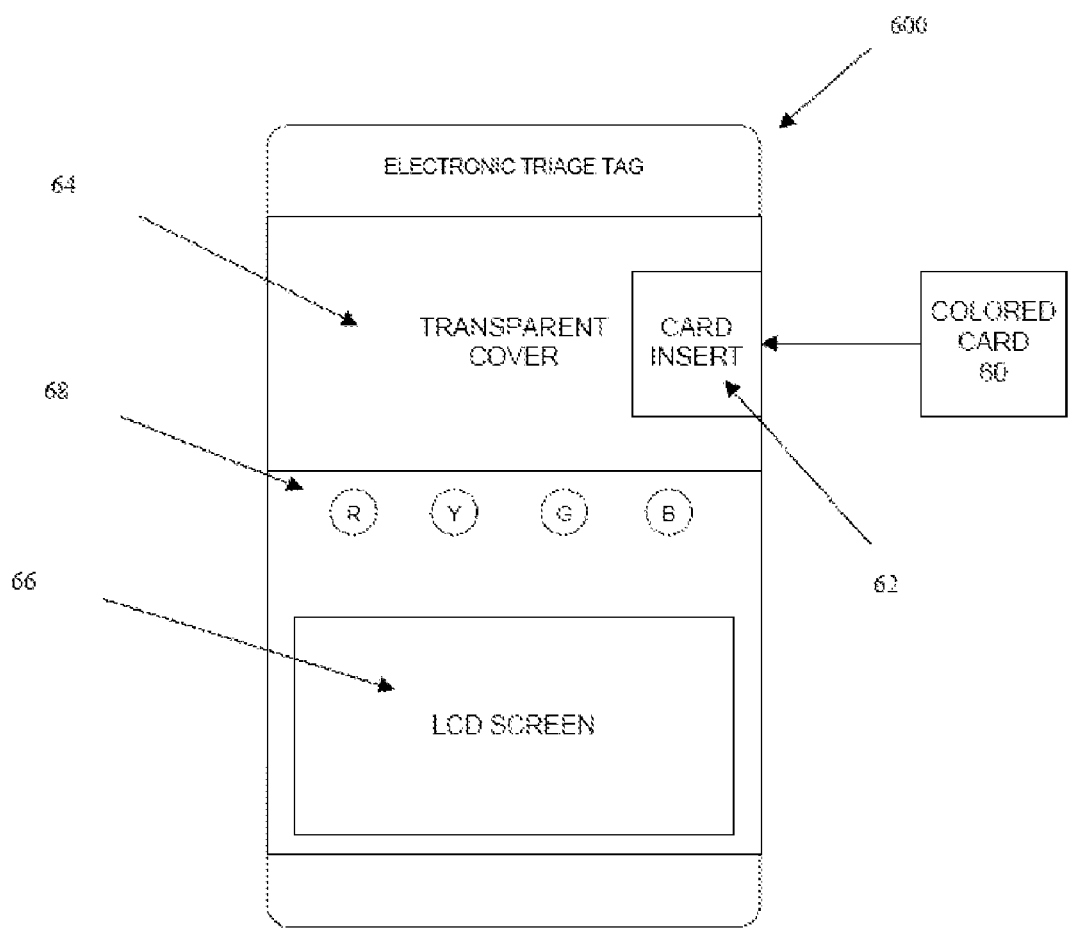
FIG. 6 is an illustration of a front view of an electronic triage tag, according to one embodiment.

Referring now to FIG. 6, there is shown a front view of an electronic triage tag 600, according to this embodiment. As shown in FIG. 6, the electronic triage tag 400 includes a colored card insertion region 62 for inserting a colored card 60, a cover strip 64 for preventing the device from being inadvertently activated, an LCD screen 66 and a series of LEDs 68 for displaying the triage status of a patient (red, yellow, green, black). The electronic triage tag 600 provides five functionalities: triage, status display, vital sign monitoring, location tracking, information display and alarm signaling.

The inclusion of card insertion region 62 overcomes a present need for medics to use complicated passwords, before setting the triage color, to prevent patients from re-triaging themselves to a higher level. For example, without the use of such passwords, a patient who is triaged by a medic at a "green" level, indicative of being the least severely injured, could easily re-triage himself to a higher level, e.g., yellow or red. This drawback is overcome through the use of color coded cards 60 for insertion by the medics into the card insertion region 62 to set the triage level of a patient.

In operation, a medic carries a number of different color cards 60 with him at an emergency scene. To set a triage level of a patient, the medic takes out an appropriately colored card 60 and inserts it into colored card insertion region 62 of the electronic tag 600. Advantageously, only the medics have access to the color cards 60, thereby precluding patients from re-triaging themselves at a later point in time.

Upon inserting the colored card 60, two events occur. First, the electronic tag 600 automatically recognizes the card color and lights up a corresponding LED 68 on the face of the tag 600 which provides a visual feedback to the medic that the electronic triage tag 600 is operating normally and (2) the triage status is wirelessly transmitted to the remote computing device 106 (see FIG. 1).

Another advantage afforded by the use of colored card inserts is the ability to continuously display a patient's triage status in the event of a battery failure. In the event of a battery failure, the card color will remain visible It is contemplated that the colored card 60 may be constructed from a variety of materials, including, but not limited to, paper cardboard and plastic.

The card color 60 can be recognized by the electronic tag 600 using any number of well known recognition techniques, including, for example, mechanical latches, light photo transmitters and receivers, IR transmitters and receivers, magnetic means, electrical circuit completion, pressure sensor buttons similar to micro piezoresistive buttons, micro switch technology used in touch screens and bar code.

Based on the foregoing specification, the invention may be implemented using computer programming or engineering techniques including computer software, firmware, hardware or any combination or subset thereof. Any such resulting program, having computer-readable code means, may be embodied or provided within one or more computer-readable media, thereby making a computer program product, i.e., an article of manufacture, according to the invention. The computer readable media may be, for instance, a fixed (hard) drive, diskette, optical disk, magnetic tape, semiconductor memory such as read-only memory (ROM), etc., or any transmitting/receiving medium such as the Internet or other communication network or link. The article of manufacture containing the computer code may be made and/or used by executing the code directly from one medium, by copying the code from one medium to another medium, or by transmitting the code over a network.

Wireless may refer to a communications, monitoring, or control system in which electromagnetic radiation spectrum or acoustic waves carry a signal through atmospheric space rather than along a wire. In wireless systems, radio frequency (RF) or infrared transmission (IR) waves may be used. Common examples of wireless equipment in use today include the Global Positioning System (GPS), cellular telephone phones and pagers, cordless computer accessories and wireless LAN (WLAN). Wi-Fi (short for "wireless fidelity") is a high-frequency wireless local area network (WLAN). Wi-Fi is specified in the 802.11b specification from the Institute of Electrical and Electronics Engineers (IEEE) and is part of a series of wireless specifications together with 802.11, 802.11a, and 802.11g. All four standards use the Ethernet protocol and CSMA/CA (carrier sense multiple access with collision avoidance) for path sharing.

One skilled in the art of computer science will easily be able to combine the software created as described with appropriate general purpose or special purpose computer hardware to create a computer system or computer sub-system embodying the methods of the invention. While various embodiments have been described above, it should be understood that they have been presented by way of example only, and not limitation. Thus, the breadth and scope of a preferred embodiment should not be limited by any of the above described exemplary embodiments, but should be defined only in accordance with the following claims and their equivalents.

What is claimed is:

1. An electronic triage tag, comprising: vital sign monitoring means, location tracking means, alarm signaling means, information display means, means for receiving a color coded card insert; a processor; a communications device coupled to the processor; a memory coupled to the processor; the memory storing instructions operable to cause the processor to: analyze patient vital sign data received from said vital sign monitoring means; determine a patient location from location data received from said location tracking means; generate an alarm condition from said analyzed patient vital sign data; initiate a communication session; establish a communication link between the communications device and a remote networking device and analyze data encoded on said color coded card insert inserted said removing means to extract a patient triage status; and communicate said extracted patient triage status over said established communication link to said remote networking device.

2. The electronic triage tag of claim 1, wherein the analysis of said data encoded on said color coded card insert is performed in accordance with a data extraction technique selected from the group comprising: mechanical latches, light photo transmitters and receivers, IR transmitters and receivers, magnetic coupling, electrical circuit completion, pressure sensor buttons, micro switches, and bar code.

3. The electronic triage tag of claim 1, wherein upon analysis of said data encoded on said color coded card insert, the electronic triage tag lights up a corresponding color coded LED on the electronic triage tag thereby providing a visual feedback that the electronic triage tag is operating normally.

* * * * *

UNITED STATES PATENT AND TRADEMARK OFFICE Certificate

Patent No. 7,629,881 B2                                                           Patented: December 8, 2009

On petition requesting issuance of a certificate for correction of inventorship pursuant to 35 U.S.C. 256, it has been found that the above identified patent, through error and without any deceptive intent, improperly sets forth the inventorship.
    Accordingly, it is hereby certified that the correct inventorship of this patent is: Tia Gao, Ellicott City, MD ((US); William E. Bishop, Baltimore, MD (US); Radford R. Juang, Irvine, CA (US); Alexander M. Alm, Rockville, MD (US); David M. White, Silver Spring, MD (US); David A. Crawford, Silver Spring, MD (US); Steven M. Babin, Greenbelt, MD (US); Jeffrey S. Chavis, Ellicott City, MD (US); Tammara M. Massey, Chevy Chase, MD (US).

Signed and Sealed this Twenty-seventh Day of March 2012.

JENNIFER MEHMOOD
*Assistant Supervisory Patent Examiner*
Art Unit 2612
Technology Center 2600